United States Patent [19]
Chadwick

[11] Patent Number: 5,089,709
[45] Date of Patent: Feb. 18, 1992

[54] TEST SYSTEM VIEWER FOR FLUORESCENCE EVALUATION

[75] Inventor: David E. Chadwick, York, Pa.

[73] Assignee: Dentsply Venture Capital Associates, L.P., York, Pa.

[21] Appl. No.: 595,504

[22] Filed: Oct. 11, 1990

[51] Int. Cl.⁵ ............................................. G01N 21/64
[52] U.S. Cl. ................................. 250/461.1; 356/51; 250/458.1
[58] Field of Search ............... 250/461.1, 459.1, 458.1; 356/51

[56] References Cited

U.S. PATENT DOCUMENTS

| | | |
|---|---|---|
| 2,502,014 | 3/1950 | Loggie . |
| 2,954,721 | 10/1957 | Voelker . |
| 3,487,210 | 12/1969 | Aubert ............................ 250/461.1 |
| 3,500,046 | 3/1970 | Caldwell ......................... 250/461.1 |
| 3,992,096 | 11/1976 | Oliveira . |
| 4,099,881 | 7/1978 | Vanden Broek et al. . |
| 4,457,894 | 7/1984 | Clark et al. . |
| 4,867,946 | 9/1989 | Gross et al. . |
| 4,934,817 | 6/1990 | Gassenhuber . |

Primary Examiner—Janice A. Howell
Assistant Examiner—Richard Hanig
Attorney, Agent, or Firm—D. James Picciano; Dale R. Lovercheck; Edward J. Hanson, Jr.

[57] ABSTRACT

A test system viewer for fluorescence evaluation has been designed to facilitate the simultaneous evaluation of multiple test samples, to provide consistency in the process for the evaluation of the fluorescence and to protect the operator from the harmful effects of the ultraviolet radiation associated with the viewer.

The viewer contains a base and a viewing shield, with the base having the fluorescent light source and an internal fluorescent standard. The viewing shield contains an internal ledge and a viewing area with a fixed viewing angle to the internal fluorescent standard. The internal ledge and the viewing angle cooperate to block ultraviolet rays from the fluorescent light source and to prevent the operator from directly viewing the light source during operation of the viewer. The use of a fixed light source, internal standard, viewing area and viewing angle insures observation consistency during the evaluation procedure.

8 Claims, 2 Drawing Sheets

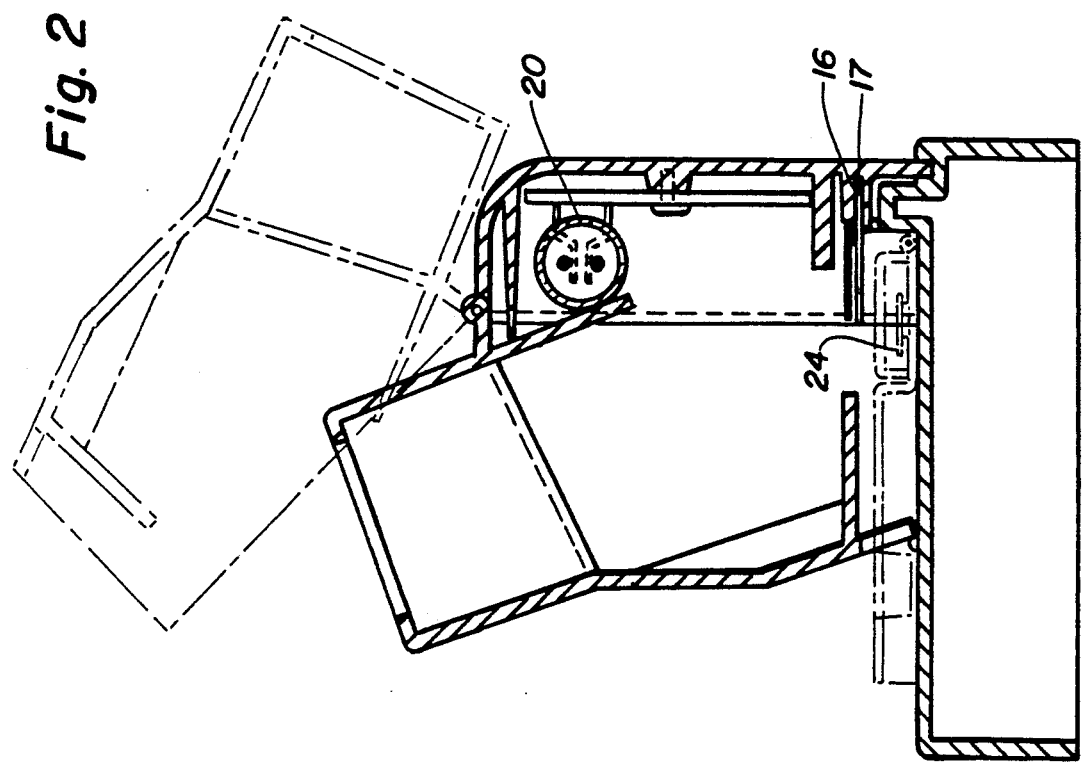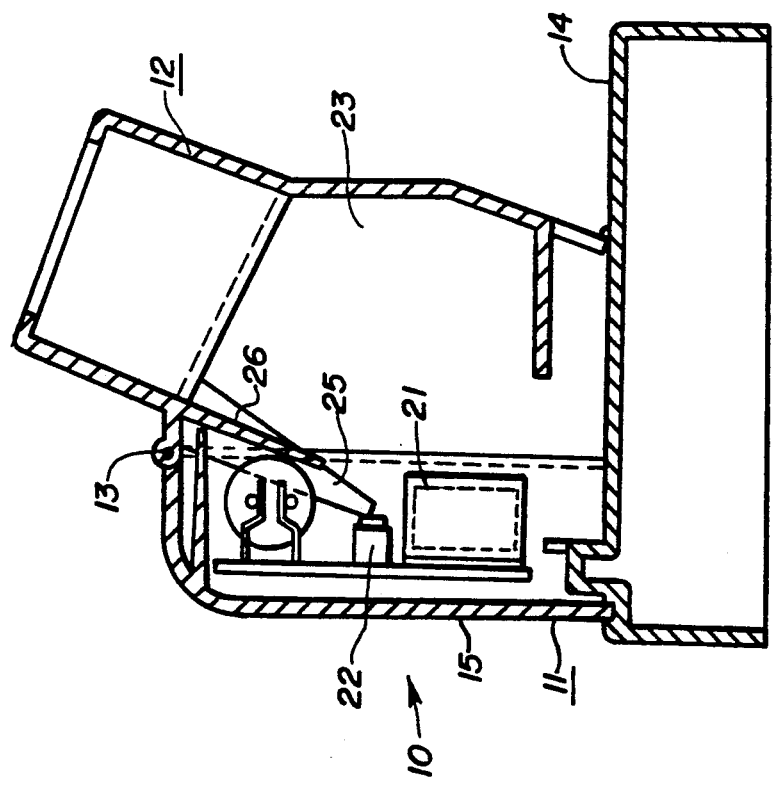

TEST SYSTEM VIEWER FOR FLUORESCENCE EVALUATION

BACKGROUND OF THE INVENTION

1. Field of the Invention

This invention relates to a test system viewer for fluorescence evaluation designed as an adjunct to single or multiple test sampling.

2. Description of the Prior Art

Evaluating a test sample for ultraviolet fluorescence simply requires exposing the test sample to a source of ultraviolet light and observing the test sample for fluorescence. An accurate quantitative determination of the sample fluorescence can be made with the use of a spectrophotometer. However, the cost of the spectrophotometer can be prohibitive and the time for individual sample preparation can be lengthy. At the other end of the scale, one can observe the presence or absence of sample fluorescence by exposing the test sample to an ultraviolet light source. This relatively simple procedure is inexpensive and rapid. However, the procedure is not quantitative because of the lack of consistency in the evaluation, i.e., variable distance of light source to sample, variable viewing angle of observer to sample, variable distance of observer to sample, variable distance between sample and standard, etc. In addition, the procedure provides little protection for the eyes of the observer from the potentially harmful effects of the ultraviolet radiation.

The above limitations have been overcome by the development of a relatively inexpensive test system viewer for the semi-quantitative determination of sample fluorescence while still protecting the human eye from ultraviolet radiation.

SUMMARY OF THE INVENTION

A test system viewer for fluorescence evaluation has been designed as an adjunct to single or multiple test sampling. Use of the viewer facilitates the simultaneous evaluation of multiple test samples, provides consistency in the evaluation of the fluorescence and protects the operator from the harmful effects of ultraviolet radiation.

The viewer is comprised of a base and a viewing shield. The base contains a fluorescent light source and an internal fluorescent standard. The viewing shield has an internal ledge and a viewing area with a fixed viewing angle to the internal fluorescent standard. The internal ledge and the viewing angle cooperate to block ultraviolet rays from the fluorescent light source and to prevent the operator from directly viewing the light source during operation of the viewer.

In a preferred embodiment, the base and the viewing shield are connected by a hinge and the viewer has a safety switch to cut power to the fluorescent light source when the viewing shield is opened during operation. In addition, the internal fluorescent standard and the test samples being evaluated for fluorescence can be positioned so that each test sample is located directly adjacent the internal standard for the evaluation.

BRIEF DESCRIPTION OF THE DRAWINGS

Further details are explained below with the help of the examples illustrated in the attached drawings in which:

FIG. 1 is a side elevation section of the viewer with the facing wall cut away.

FIG. 2 is a side elevation section of the viewer with section being just short of the mid line through the viewer.

DESCRIPTION OF THE PREFERRED EMBODIMENT

Figure 3:
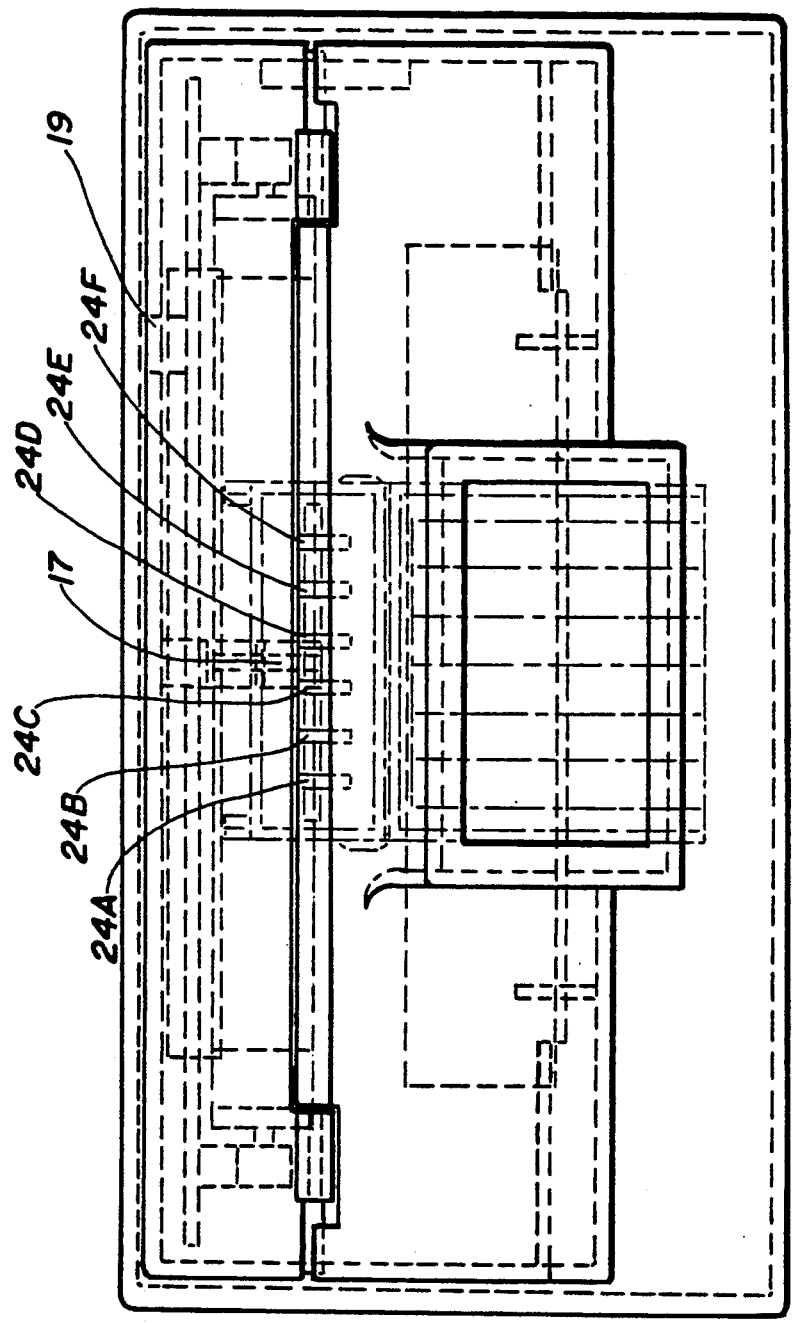
FIG. 3 is a top plan view of the viewer.

FIG. 1 shows that in the preferred embodiment the viewer 10 has a base 11 and a viewing shield 12 attached to the base by a hinge 13. The base has a platform 14 upon which the sample to be analyzed rests and an upright back 15 which forms a right angle with the rear of the platform.

Referring to FIG. 2 it will be seen that the back 15 contains a shelf 16 that has an internal positive standard 17 attached thereto, a longwave ultraviolet lamp 20, a power switch 21 (FIG. 1), a safety switch 22, and a viewing area 23. The shelf 16 is designed so that an internal standard 17 may be attached to the shelf and compared to the test sample 24. In addition, the shelf 16 is above and over the platform 14 enabling a test sample or samples 24C and 24D to be positioned directly adjacent the internal standard during the analysis, see FIG. 3.

The longwave ultraviolet lamp 20 is controlled by the power switch 21 located on the side of the back 15. The power connection is shown at 19 in FIG. 3. Directly above the power switch 21 and interior thereto is a safety switch 22 designed to cut power to the lamp when the viewing shield 12 is opened during operation. The safety switch 22 is released to shut off the power when the finger extension 25 which is an integral part of the shield 12 is moved from the safety switch 22 as the shield is opened. In this way, the operator will not be directly exposed to the ultraviolet rays during operation of the viewer. The viewing shield has also been designed to contain an internal ledge 26 that blocks the ultraviolet rays and prevents the operator from directly viewing the ultraviolet lamp during analysis. In addition, the shield has a viewing area 23 which has been designed at an angle in cooperation with the viewing shield ledge to prevent the operator form directly viewing the ultraviolet lamp.

In addition to the safety features incorporated with regard to the ultraviolet rays, the fixed angle of the viewing area and the permanent location of the internal standard result in a consistent measuring system whereby the operator's eyes are always located at this same angle and approximate distance from the test sample during the analysis. As mentioned above, the base and viewing shield are attached by a hinge at the top of the base and viewing shield. It is further note worthy that lenses are not required or shown in the preferred embodiment although they could be incorporated.

EXAMPLE

This example describes how the viewer is used in conjunction with a test for the presence of the enzyme elastase in a given solution. The test employs enzyme test strips, a test strip carrier or incubator box and a timer. The test strips and carrier are the subject of a separate patent application, U.S. patent application Ser. No. 595,52, the contents of which are hereby incorporated by reference. The timer is the subject of patent application, U.S. patent application Ser. No. 595,893, the contents of which are also hereby incorporated by reference.

Test strips were prepared from filter paper. Whatman 541 filter paper (0.16 mm in thickness) was sandwiched between two plastic portions so that more than one mm of the filter paper was exposed and one mm of the filter paper was between the two plastic portions. The filter paper was then impregnated with an elastase enzyme substrate and the test strips cut to size.

The filter paper was impregnated with substrate by wetting the filter paper exposed tips of the test strips in 0.85 millimolar methoxysuccinyl-alanine-alanine-proline-valine-7-amino-4-trifluoromethyl coumarin (Lot # AP65 from Enzyme Systems Products, Livermore, California) in elastase substrate buffer (0.5 M NaCl, 0.1 M HEPES(N-2-hydroxyethyl-piperazine N-2-ethanesulfonic acid), pH 8.14). The impregnated filter paper was allowed to dry overnight. Following drying, test strips of eight mm in length and two mm in width were cut so that one mm of impregnated filter paper was exposed and available for absorption of biological fluid.

The impregnated test strips were used to test for elastase as follows. An elastase test solution was prepared by dissolving 1.2 mg of elastase (Biozyme, San Diego, CA) in elastase substrate buffer described above so that a final concentration of 2 mg/ml elastase enzyme was obtained. The stock solution and serial dilutions (50 to 5 ug/ml elastase) were tested.

The test strips were tested in an assay in such a way that final evaluations of a maximum of six test strips were made no less than four and no more than eight minutes after exposure to the test enzyme. Thus, a first test strip, impregnated with methoxysuccinyl-alanine-alanine-proline-valine-7-amino-4-trifluoromethyl coumarin was inserted into an elastase test solution for 15 seconds. When the first test strip was inserted into the solution, the start button of the timer was depressed, a short beep was sounded, the strip indicator flashed the character # and the number 1 was displayed on the display panel. Simultaneously with the depressing of the start button, the running clock displayed 3 minutes and 45 seconds, the time remaining in the test mode for the collection of test samples. When the running clock reached 3:30, a single beep sounded, the character # disappeared from view and the number 1 ceased to flash but was continuously displayed. At this time, the first test strip, containing approximately 0.9 ul of elastase test solution, was removed from the test solution, attached to the adhesive layer in an incubator box and allowed to incubate at room temperature. The incubator box had been previously attached to the timer via the timer's carrier attachment plate side slots and protuberances.

A second test strip was inserted into the elastase test solution for 15 seconds. When the second test strip was inserted into the solution, the start button was depressed, a short beep was sounded, the strip indicator flashed the character # and the number 2 was displayed on the display panel. When the second test strip was inserted into the solution and the start button depressed, the running clock displayed 3 minutes and 15 seconds, the time remaining in the test mode for the collection of test samples. When the running clock reached 3:00, a single beep sounded, the character # disappeared from view and the number 2 ceased to flash but was continuously displayed. At this time, the second test strip was removed from the test solution, attached to the adhesive layer in an incubator box and allowed to incubate at room temperature.

The collection and timing procedure was repeated for test strips 3, 4, 5 and 6. When the sixth test strip was inserted into the solution and the start button depressed, the running clock displayed 1 minute and 15 seconds. When the clock reached 1:00, a double beep sounded, the character # disappeared from view and the number 6 ceased to flash but was continuously displayed. The maximum number of samples had been collected with 1 minute remaining in the test or collection phase and the timer automatically switched to the view phase. The running clock displayed 3:45 which was the time remaining for the incubation of the sixth test strip so that all six strips would have incubated for at least four minutes and be evaluated in less than eight minutes. At the end of the 3 minute and 45 second view phase, a beep and chime alarm sounded and the running clock displayed 1:30, the time remaining in the evaluation phase so that all six strips would be evaluated between six and one-half and eight minutes, i.e., within the predetermined four to eight minute window.

The six test strips attached to the adhesive strip in the incubator box were evaluated for fluorescence in a viewer or viewing chamber equipped with a longwave ultraviolet lamp (General Electric F4T5/BLB). The lamp was mounted so that it illuminated equally the test strips and a positive internal standard.

Reactive elastase was determined by measuring a fluorescing leaving group which was released by the hydrolytic action of elastase upon the substrate and visually assayed in the viewing chamber. After the incubation period each test strip was evaluated for fluorescent intensity. A bright green fluorescence, indicative of substrate cleavage with release of 7-amino-4-trifluoromethyl coumarin, indicated the presence of the elastase enzyme. Thus, a test strip which fluoresced with the brightness and intensity equal to or greater than the internal standard was recorded as a positive response, indicative of the elastase enzyme. In the absence of elastase, the test strip fluoresced a dull blue-purple, indicative of intact substrate. After one minute and 30 seconds, the alarm of the timer sounded a continuous alarm indicating the end of the evaluation phase and shut itself off.

It should be noted that the semi-quantitation of test strip fluorescence was possible according to the following scale. A zero concentration of elastase was indicated by a dull blue-purple color. Low concentrations of elastase caused the paper strip to show light blue under the ultra-violet light, moderate concentrations of elastase caused a green-blue color to develop, higher concentrations caused a green color, and even higher concentrations caused a bright green color.

While the present embodiment of the invention and method of practicing the same have been illustrated and described, it will be recognized by those skilled in the art that this invention may be otherwise variously embodied and practiced within the scope of the following claims.

What is claimed is:

1. A viewer for the evaluation of fluorescence, comprising:
   a. a base having
      (1). a fluorescent light source and
      (2). an internal fluorescent standard and
   b. a viewing shield having
      (1). an internal ledge and
      (2). a viewing area with a viewing angle to the internal fluorescent standard, wherein the internal ledge and the viewing angle cooperate to block ultraviolet rays from the fluorescent light source and to prevent an operator from directly viewing the light source during operation of the viewer.

2. The viewer of claim 1 wherein the internal fluorescent standard and test samples being evaluated for fluorescence can be positioned so that each test sample is located directly adjacent the internal standard for the evaluation.

3. The viewer of claim 2 wherein the fluorescent light source is positioned at a fixed distance from the internal fluorescent standard and the test samples.

4. The viewer of claim 2 wherein the internal fluorescent standard is fixed to the viewer.

5. The viewer of claim 1 wherein the viewing shield is hingedly attached to the base.

6. The viewer of claim 5 further comprising a safety switch to cut power to the fluorescent light source when the viewing shield is opened during operation.

7. The viewer of claim 1 wherein said viewer does not have a lens.

8. A viewer for the evaluation of fluorescence, comprising:
   a. a base having
      (1). an ultraviolet light source,
      (2). an internal fluorescent standard and
   b. a viewing shield connected to said base by a hinge, said shield extending above said base and having an internal ledge, said internal ledge being adapted to block ultraviolet light rays from the said light source whereby an operator is prevented from directly viewing said light source.

* * * * *